United States Patent
Pavcnik

(10) Patent No.: US 8,257,429 B2
(45) Date of Patent: Sep. 4, 2012

(54) BIOMEDICAL VALVE DEVICES, SUPPORT FRAMES FOR USE IN SUCH DEVICES, AND RELATED METHODS

(75) Inventor: Dusan Pavcnik, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 704 days.

(21) Appl. No.: 11/842,363

(22) Filed: Aug. 21, 2007

(65) Prior Publication Data

US 2008/0046071 A1   Feb. 21, 2008

Related U.S. Application Data

(60) Provisional application No. 60/822,963, filed on Aug. 21, 2006.

(51) Int. Cl.
*A61F 2/24*   (2006.01)
*A61F 2/86*   (2006.01)

(52) U.S. Cl. ............... 623/1.24; 623/1.26; 623/2.14

(58) Field of Classification Search ............ 623/1.26, 623/1.13, 1.1, 1.14, 1.15, 1.16, 1.24, 1.3, 623/1.31, 2.12–2.19, 2.38, 2.1
See application file for complete search history.

(56) References Cited

U.S. PATENT DOCUMENTS

| | | |
|---|---|---|
| 4,218,782 A | 8/1980 | Rygg |
| 4,275,469 A | 6/1981 | Gabbay |
| 4,470,157 A | 9/1984 | Love |
| 4,580,568 A | 4/1986 | Gianturco |
| 4,666,442 A | 5/1987 | Arru et al. |
| 4,759,758 A | 7/1988 | Gabbay |
| 5,411,552 A | 5/1995 | Anderson |
| 5,545,215 A | 8/1996 | Duran |
| 5,667,523 A | 9/1997 | Bynon et al. |
| 5,855,601 A | 1/1999 | Bessler |
| 5,957,949 A | 9/1999 | Leonhardt |
| 6,126,686 A | 10/2000 | Badylak et al. |
| 6,231,598 B1 | 5/2001 | Berry et al. |
| 6,299,635 B1 | 10/2001 | Frantzen |
| 6,299,637 B1 | 10/2001 | Shaplian |
| 6,312,465 B1 | 11/2001 | Griffin et al. |
| 6,371,983 B1 | 4/2002 | Lane |
| 6,375,679 B1 | 4/2002 | Martyn et al. |

(Continued)

FOREIGN PATENT DOCUMENTS

WO   WO0154625   8/2001

OTHER PUBLICATIONS

Office Action issued by the United States Patent and Trademark Office on Jul. 30, 2009 in U.S. Appl. No. 10/903,907.

*Primary Examiner* — Corrine M McDermott
*Assistant Examiner* — Suba Ganesan
(74) *Attorney, Agent, or Firm* — Buchanan Nipper

(57) ABSTRACT

Biomedical valve devices, support frames for use in such devices, methods of making such devices, and methods of treating animals, including humans, for valve-related conditions are described. The biomedical valve devices can includes a native tissue valve attached to a support frame or a tissue attached to a support frame in a manner to form a valve. The tissue valve or tissue can be autogenous to the animal being treated.

20 Claims, 9 Drawing Sheets

U.S. PATENT DOCUMENTS

| | | |
|---|---|---|
| 6,440,164 B1 | 8/2002 | DiMatteo |
| 6,458,153 B1 | 10/2002 | Bailey |
| 6,464,720 B2 | 10/2002 | Boatman et al. |
| 6,494,909 B2 | 12/2002 | Greenhalgh |
| 6,508,833 B2 | 1/2003 | Pavcnik |
| 6,582,464 B2 | 6/2003 | Gabbay |
| 6,685,739 B2 | 2/2004 | DiMatteo |
| 7,025,780 B2 | 4/2006 | Gabbay |
| 7,125,418 B2 | 10/2006 | Duran et al. |
| 7,128,759 B2 | 10/2006 | Osborne |
| 7,153,324 B2 | 12/2006 | Case |
| 2001/0039450 A1 | 11/2001 | Pavcnik |
| 2002/0032481 A1* | 3/2002 | Gabbay ........................ 623/2.11 |
| 2003/0055492 A1 | 3/2003 | Shaolian et al. |
| 2003/0153974 A1 | 8/2003 | Spenser et al. |
| 2004/0102855 A1 | 5/2004 | Shank |
| 2004/0210306 A1 | 10/2004 | Quijano |
| 2005/0085900 A1 | 4/2005 | Case |
| 2005/0096736 A1 | 5/2005 | Osse |
| 2005/0113910 A1 | 5/2005 | Paniagua |
| 2005/0137676 A1 | 6/2005 | Richardson |
| 2005/0137691 A1* | 6/2005 | Salahieh et al. ............. 623/2.11 |
| 2005/0143807 A1 | 6/2005 | Pavcnik |
| 2006/0058872 A1* | 3/2006 | Salahieh et al. ............. 623/2.18 |
| 2006/0106454 A1 | 5/2006 | Osborne |
| 2006/0253188 A1 | 11/2006 | Case |
| 2007/0038295 A1 | 2/2007 | Case |
| 2007/0043431 A1 | 2/2007 | Melsheimer |
| 2007/0227518 A1 | 10/2007 | Case |

* cited by examiner

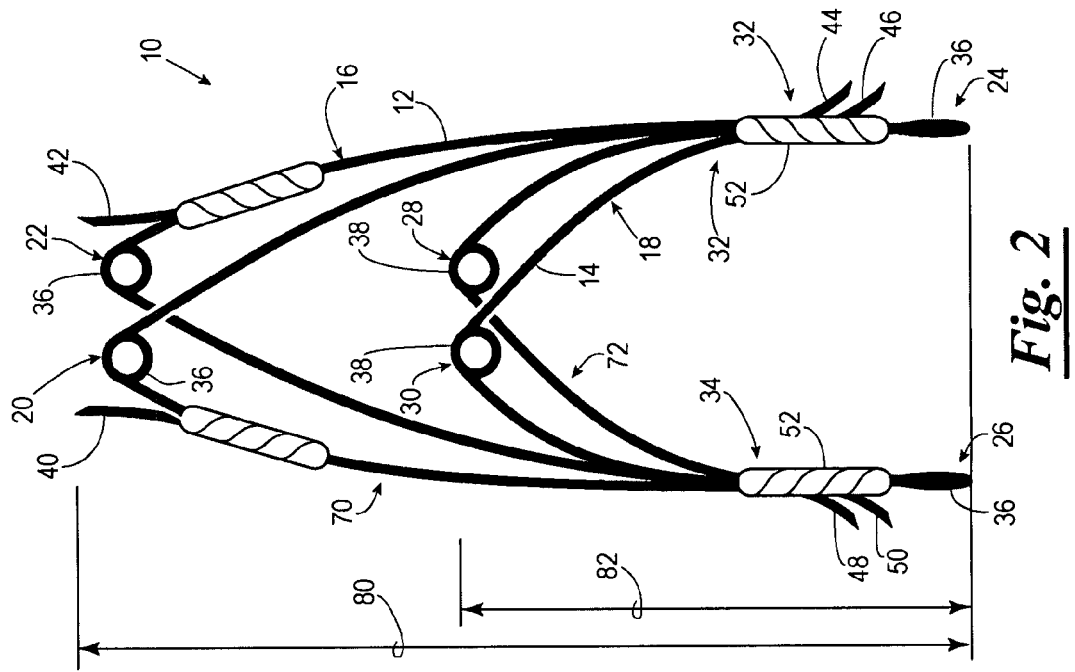
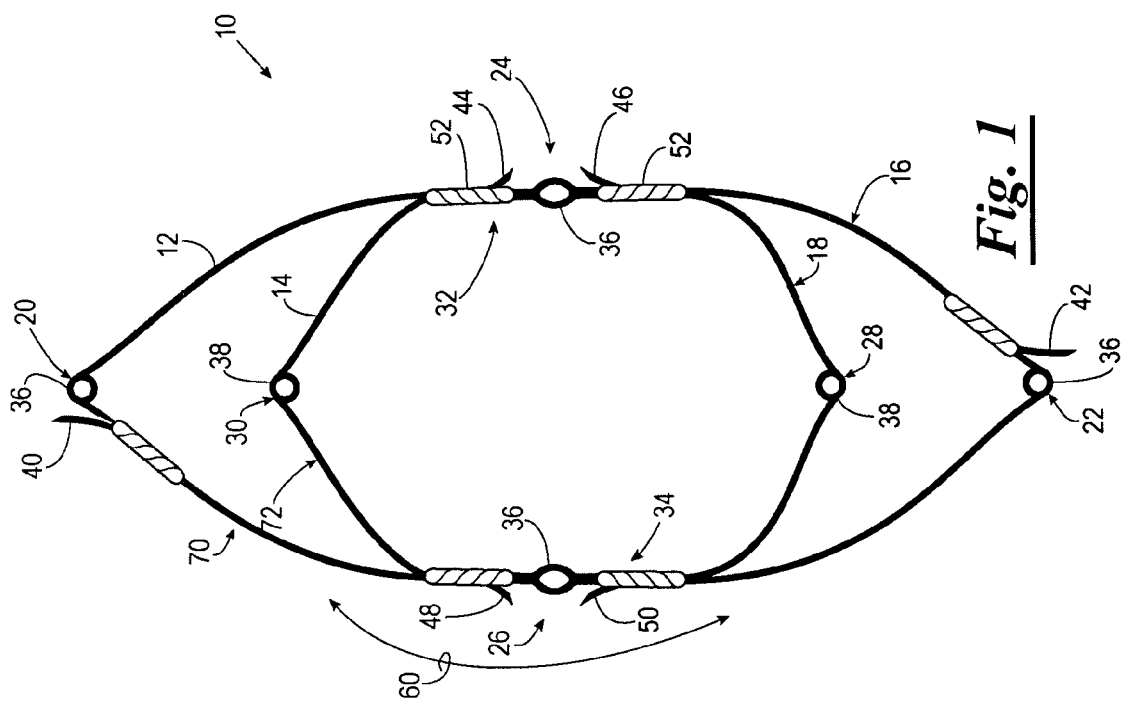

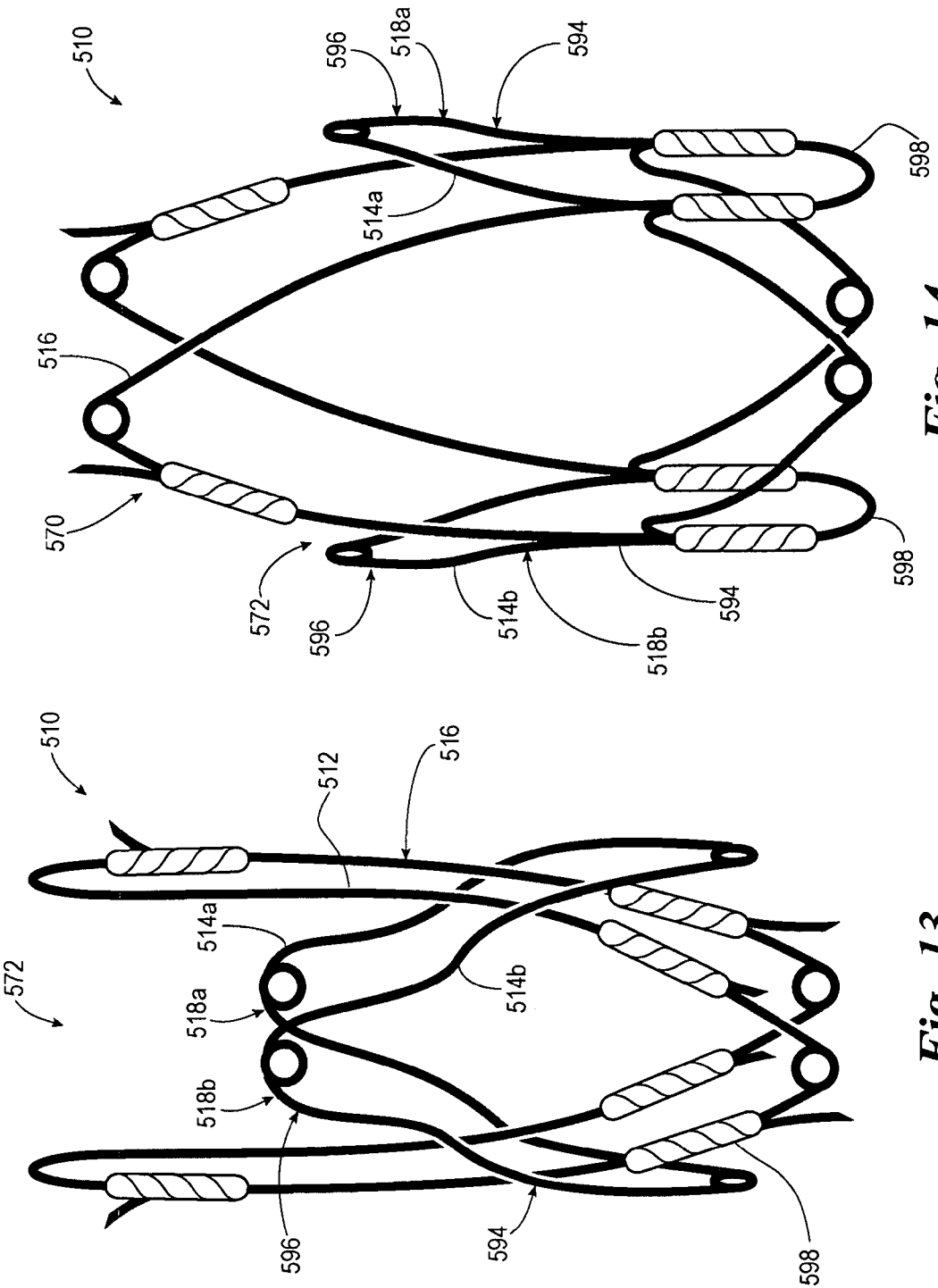

BIOMEDICAL VALVE DEVICES, SUPPORT FRAMES FOR USE IN SUCH DEVICES, AND RELATED METHODS

CROSS-REFERENCE TO RELATED APPLICATION

This application claims priority to U.S. Provisional Application Ser. No. 60/822,963, filed on Aug. 21, 2006, the entire contents of which are hereby incorporated into this disclosure.

FIELD

The disclosure relates, generally, to the field of medical devices and associated methods of making medical devices and methods of treating animals, including humans, with medical devices. More particularly, the disclosure relates to valve devices that can be used to affect the flow of fluid through a body vessel.

BACKGROUND

Many vessels in animal bodies transport fluids from one bodily location to another. Frequently, fluid flows in a unidirectional manner along the length of the vessel. In some vessels, such as mammalian veins, natural valves are positioned along the length of the vessel and act as one-way check valves that open to permit the flow of fluid in the desired direction and close to substantially prevent fluid flow in a reverse direction, i.e., retrograde flow. These natural valves can change between open and closed positions in response to a variety of circumstances, including changes in the cross-sectional shape of the vessel and the fluid pressure within the vessel.

While natural valves may function without failure for an extended time, some may lose effectiveness, which can lead to physical manifestations and pathology. For example, venous valves are susceptible to becoming insufficient due to one or more of a variety of factors. For example, vein walls may become stretched or weakened in localized areas, affecting the ability of the valve leaflets within the affected areas to close. Furthermore, natural valve leaflets are relatively fragile and may become damaged, such as by formation of thrombus and scar tissue, which may also affect the ability of the valve leaflets to close. Ultimately, damaged venous valves may lead to venous valve insufficiency, which can produce a variety of clinical manifestations, including swelling of the lower leg, discomfort, and ulcers in the legs and ankles that are difficult to heal. Valve insufficiency patients are often unable to withstand even short periods of standing.

Current treatments for venous valve insufficiency include the use of compression stockings that are placed around the leg of a patient in a effort to force the vessel walls radially inward to restore valve function. Surgical techniques can be employed in which valves can be bypassed, repaired, such as by valvuloplasty, or replaced with artificial valves or autogenous sections of veins having competent valves. The art has recently expanded to include prosthetic valves that are implantable by minimally invasive techniques, including catheter-based deployment of self-expandable valve devices. In these devices, a graft member is typically attached to a support frame in a manner that forms some type of valve that is able to selectively open and close in response to various environmental factors, such as changes in fluid pressure, within a body vessel. For example, the graft member can be in the form of one or more leaflets that are attached to a support frame and movable between first and second positions. In a first position, the valve is open and allows fluid flow to proceed through a vessel in a first direction. In a second position, the valve is closed to prevent fluid flow in a second, opposite direction, i.e., retrograde flow. Examples of this type of prosthetic valve are described in commonly owned U.S. Pat. No. 6,508,833 to Pavcnik for a MULTIPLE-SIDED INTRALUMINAL MEDICAL DEVICE, United States Patent Application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety.

The use of autogenous tissue in a valve device has the advantage of avoiding some materials-based concerns that must be taken into consideration when developing a prosthetic valve that includes a graft member formed of non-autogenous materials, such as non-natural materials and natural, non-autogenous materials. To date, however, many artisans believed that the drawbacks of using autogenous tissue in a valve device outweighed the benefits. For example, the use of autogenous tissue requires additional procedures in a treatment regimen, including harvesting of the tissue and fashioning of the tissue into a useable valve device, that many believe are too time-consuming and complicated to form the basis of a dependable treatment regimen.

As a result, there remains a need in the art for improvements relating to autogenous biomedical valves and related methods.

SUMMARY OF EXEMPLARY EMBODIMENTS

The invention provides biomedical valve devices that are suitable for use in treating a variety of conditions, including venous disease. Support frames that provide a scaffolding onto which a tissue valve and/or tissue can be attached to form a biomedical valve device are described. A preexisting tissue valve can be placed on the support frame or a non-valve tissue can be placed on the support frame in a manner to form a valve.

A support frame according to a first exemplary embodiment comprises first and second interconnected frame members. The first frame member defines a first closed circumference and has a first axial length. The second frame member defines a second closed circumference and a second axial length. The second closed circumference is smaller than the first closed circumference and the second axial length is shorter than the first axial length. The first and second frame members are joined at proximal base portions and substantially free of each other at distal apical portions.

In one exemplary embodiment, the second frame member includes a plurality of arms, each of which includes a base portion and an upper portion separated by an angle. In another exemplary embodiment, the second frame member includes a lower portion that joins two or more arms.

Biomedical valve devices are also described. Valve devices according to exemplary embodiments include a support frame according to the invention and a tissue valve attached to the support frame. Valve devices according to other exemplary embodiments include a support frame according to the invention and a tissue attached to the support frame in a manner to form a valve. Exemplary embodiments include a native venous valve attached to a support frame according to the invention. Another exemplary embodiment comprises a section of an body vessel, such as a vein, attached to a support frame according to the invention. Attachment of a tissue valve or a tissue to form a valve can be accomplished using sutures or other suitable fasteners. Exemplary embodiments include a tissue valve or a tissue attached to a support frame according to the invention using barbs associated with the support frame, either in conjunction with or in the absence of other means for attaching the tissue valve or tissue to the support frame.

Methods of making biomedical valve devices are also described. An exemplary method comprises the steps of providing a support frame according to the invention and providing a tissue valve. Another step comprises attaching the tissue valve to the support frame. In one exemplary method, the tissue valve comprises a native venous valve. In another exemplary embodiment, the tissue valve comprises a venous valve harvested from the same patient into which the biomedical valve device is intended to be implanted. In this embodiment, the biomedical valve device comprises an autogenous biomedical valve device. In alternative embodiments, a tissue, such as a portion of a body vessel, is attached to the support frame in a manner to form a valve.

Methods of treating animals, including human and non-human animals alike, for valve-related conditions are also described. A exemplary method comprises the steps of harvesting a tissue valve from the patient and providing a support frame according to the invention. Another step comprises forming an autogenous biomedical valve device by attaching the tissue valve to the support frame. Any suitable method of forming a biomedical valve device according to the invention can be used for this step. Another step comprises loading the biomedical valve device into a suitable delivery system. Another step comprises advancing the biomedical valve device, loaded on the delivery system, to a point of treatment within a body vessel. Another step comprises deploying the biomedical valve device using a technique appropriate for the selected delivery system. Another step comprises withdrawing the delivery step from the body vessel. In alternative embodiments, a tissue, such as a portion of a body vessel, is harvested from the patient and attached to the support frame in a manner to form a valve.

Additional understanding of the invention can be obtained with review of the detailed description of exemplary embodiments, below, and the appended drawings illustrating various exemplary embodiments.

BRIEF DESCRIPTION OF THE DRAWINGS

FIG. 1 is an illustration of a support frame according to a first exemplary embodiment shown in a flattened configuration.

FIG. 2 is a side view of the support frame of FIG. 1 shown in a second configuration.

FIG. 13 is a side view of a support frame according to a sixth exemplary embodiment.

FIG. 14 is a second side view of the support frame illustrated in FIG. 13.

DETAILED DESCRIPTION OF EXEMPLARY EMBODIMENTS

Figure 4:
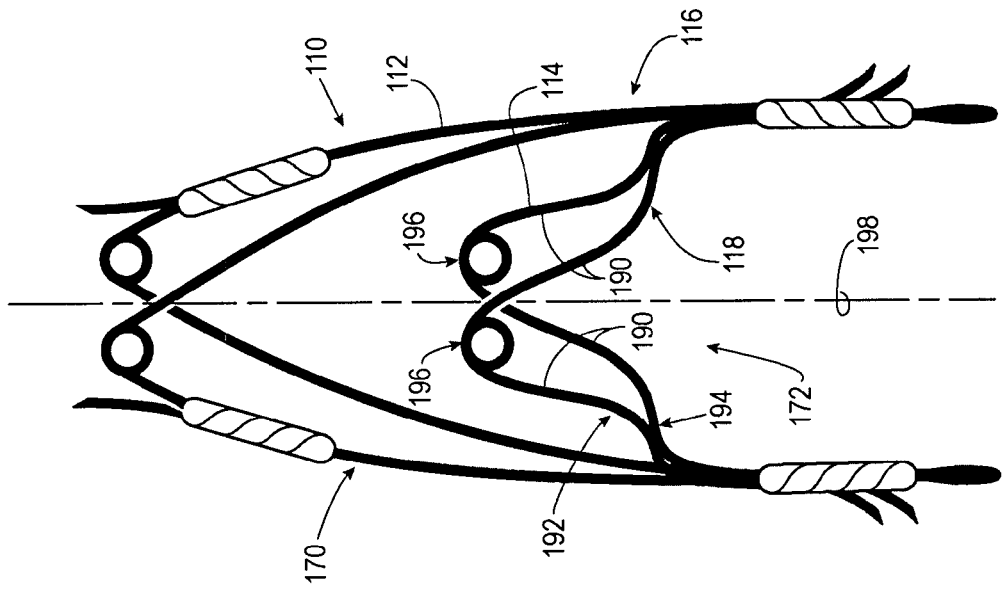
FIG. 4 is a side view of the support frame of FIG. 3 shown in a second configuration.

The following detailed description and the appended drawings describe and illustrate exemplary embodiments of the invention solely for the purpose of enabling one of ordinary skill in the relevant art to make and use the invention. As such, the description and illustration of these embodiments are purely exemplary in nature and are in no way intended to limit the scope of the invention, or its protection, in any manner.

FIGS. 1 and 2 illustrate a support frame 10 according to a first exemplary embodiment. The support frame comprises first 12 and second 14 interconnected frame members. In this embodiment, each of the frame members 12, 14 comprises a wire member formed into a closed circumference from a single piece of material. The closed circumference 16 defined by the first frame member 12 has an overall length that is greater than the overall length of the closed circumference 18 defined by the second frame member 14. As such, the second frame member 14 is essentially disposed within the closed circumference 16 of the first frame member 12 when the support frame 10 is in a flattened configuration, such as the view illustrated in FIG. 1.

In the illustrated embodiment, each of the frame members 12, 14 comprises a simple wire frame support, which is described in detail in U.S. Pat. No. 6,508,833 to Pavcnik et al. for a MULTIPLE-SIDED INTRALUMINAL MEDICAL DEVICE, the entire contents of which is hereby incorporated by reference for the purpose of describing suitable frame members for use in support frames according to the invention.

The first frame member 12 comprises apical bends 20, 22 and lateral bends 24, 26. The second frame member 14 comprises apical bends 28, 30 and lateral bends 32, 34. The first frame member 12 includes a coil 36 at each bend 20, 22, 24, 26. The presence of coils enhances the flexibility of the support frame 10 and can provide a point for anchoring tissue or other material to the frame 10. The second frame member 14 includes coils 38 at apical bends 28, 30. Coils can also be included at lateral bends 32, 34 or, as in the illustrated embodiment, these coils can be eliminated.

Barbs can be included at various locations to facilitate anchoring of the support frame 10 in a body vessel and/or attachment of tissue or other material to the frame 10. The illustrated embodiment includes apical barbs 40, 42 disposed on opposing struts of the first frame member 12. Lateral barbs 44, 46, 48, 50 can be disposed near the lateral bends 24, 26 of the first frame member 12 and/or the lateral bends 32, 34 of the second frame member 14. As best illustrated in FIG. 1, these barbs 44, 46, 48, 50 can be formed by cutting the second frame member 14 at the lateral bends 32, 34. It is noted, though, that separately attached members can also be used to form lateral barbs.

As best illustrated in FIG. 1, the support frame 10 according to the first exemplary embodiment is formed simply by interconnecting the first 12 and second 14 frame members. Various cannulae 52 disposed at various locations can be used to join the frame members 12, 14. In the illustrated embodiment, cannulae 52 are disposed near each of the lateral bends 24, 26, 32, 34. Each cannulae receives a portion of each frame member 12, 14 and is crimped, welded, soldered or otherwise fixed to form a connection between the members 12, 14. While cannulae are illustrated as a means for connecting the first 12 and second 14 frame members, it is expressly understood that any suitable means for connecting members together can be used, including adhesives, direct soldering of the first frame member 12 to the second frame member 14, and other suitable means for connecting. Cannulae 52 or other suitable means for connecting are also used to join ends of a wire or other material used to form each of the frame members 12, 14. Joining of blunt ends of a wire or other material can also be used.

The support frame 10 is placed in a second configuration, illustrated in FIG. 2, by advancing a apical bends 20, 22 of the first frame member 12 toward each other, which results in apical bends 28, 30 of the second frame member 14 being similarly advanced toward each other. This transformation is represented by arrow 60 in FIG. 1. The resulting second configuration is illustrated in FIG. 2. The second configuration substantially represents the form the support frame 10 would take within a body vessel following deployment. It is the configuration the support frame 10 would be in prior to loading in a delivery system to effect such deployment in a body vessel, as will be described in detail below. Immediately prior to loading into a delivery system, the support frame, along with any attached tissue valve or tissue fashioned into a valve, the support frame can be compressed into a low-profile configuration suitable for placement within the selected delivery system.

When deployed in a lumen of a vessel, the support frame 10 in the second configuration exerts a radially outward force on the interior wall of the vessel. The bending stresses introduced to the frame 10 by the folding required to form the second configuration apply force radially outward against the vessel wall to hold the frame in place and prevent vessel closure. Absent any significant plastic deformation occurring during folding and deployment, the second configuration, when not in the vessel or subject to other constraining means, will at least partially return to the first configuration illustrated in FIG. 1, although some deformation can occur depending on the material used. It is also possible to plastically deform the frame 10 into the second configuration, such that it does not unfold when restraint is removed. This might be particularly desirable if the device is made from nitinol or a superelastic alloy.

As best illustrated in FIG. 2, the support frame 10 includes vessel 70 and valve 72 support portions. The vessel support portion 70 is defined by the circumference 16 of the first frame member 12 when the support frame 10 is in the second configuration. Similarly, the valve support portion 72 is defined by the circumference 18 of the second frame member 14 when the support frame 10 is in the second configuration. Because the circumference 16 of the first frame member 12 is greater than the circumference 18 of the second frame member 14, the vessel support portion 70 has an axial length 80 that is greater than the axial length 82 of the valve support portion 72, as measured from a hypothetical line 84 that connects lateral bends 24, 26 of the first frame member 12 when the support frame 10 is in the second configuration. In use, the vessel support portion 70 provides support to the portion of the vessel in which the support frame 10 is implanted and the valve support portion 72 provides a structure onto which a tissue valve or other tissue can be attached to form a biomedical valve device, as will be described in more detail below. This structural and spatial relationship between the vessel 70 and valve 72 support portions ensures that a valve disposed or formed on the valve support portion 72 is positioned within an area of a body vessel that is supported by the vessel support portion 70 when a biomedical valve that incorporates the support frame 10 is implanted in a body vessel. This is believed to be advantageous at least because it provides a separation between the vessel wall and the valve.

The support frame 10 is made of resilient material, preferably metal wire formed from stainless steel or a superelastic alloy, such as nitinol. Other materials, such as polymeric and resorbable materials, can also be used. Indeed, any suitable material can be used to form a support frame according to the invention. The material chosen for a specific support frame according to a particular embodiment need be capable of providing the desired support to the vessel and to the valve. The material should be biocompatible or be capable of being rendered biocompatible. The support frame 10 and/or the individual frame members 12, 14 could also be formed by punching, cutting or otherwise forming the item from a solid piece of material. For example, the support frame 10 could be laser cut from a nitinol tube, as is known in the art.

Certain features of the support frame can be modified and/or optimized based upon the characteristics of the selected material. For example, instead of using coils, such as coils 36 and 38 of the embodiment illustrated in FIGS. 1 and 2, a simple bend, such as a substantially orthogonal bend, may be more appropriate if the frame is formed of nitinol or another superelastic alloy because the formation of certain types of bends, such as coils, may actually decrease fatigue life of a superelastic material. Other alternative bend structures, including outward-projecting fillets and inward-projecting fillets comprising a series of curves, can be used and may be appropriate for certain types of materials. Fillets are well known in the stent art as a means for reducing stresses in bends. In any particular embodiment, the specific structure chosen for bends in the frame members 12, 14 should be one that minimizes bending fatigue for the material of which the support frame 10 is formed. If this construction is used, certain features of the illustrated embodiment, such as the various coils, may not be necessary.

While round wire is depicted in the figures, other types, such as wire having flat, square, triangular, D-shaped, trapezoidal, and delta-shaped cross-sectional profiles may be used to form the frame 10. Indeed, wire having any suitable cross-sectional shape can be used. Furthermore, while each of the first 12 and second 14 frame members of the support frame 10 illustrated in FIGS. 1 and 2 have four sides of approximately equal length, it is expressly understood that frames with sides of different lengths and frames of any polygonal shape, such as pentagons hexagon, and octagon shapes, can also be used.

The cross-sectional diameter of the wire selected will depend on the size of the medical device and the application. Wire that is too stiff can damage the vessel, not conform well to the vessel wall, and increase the profile of the device when loaded in a delivery system prior to deployment. Wire that is not sufficiently stiff may not allow a valve disposed or formed on the valve support portion 72 to function as desired. An appropriate diameter can be selected by those skilled in the art based on various considerations, including the desired profile of a delivery system into which a biomedical valve device incorporating the support frame 10 will be loaded, the vessel within which the device is intended to be used, and the type of tissue valve and/or tissue that will be attached to the support frame 10 during use. It is expressly understood and appreciated that material of different diameters could be used for different portions of the support frame. For example, the first frame member 12 could be formed of wire having a first diameter and the second frame member 14 could be formed of wire having a second, different diameter. This may be advantageous if different support characteristics are desired for the vessel 70 and valve 72 support portions. It is also expressly understood and appreciated that material that has a varying diameter over its length could be used to form the support frame 10 or portions of the support frame 10. For example, one or both frame members 12, 14 could be formed of a wire that has a first diameter along portions of its length and a second, different diameter along other portions of its length. This construction could be used to place wire with a larger diameter in portions of a frame member 12, 14 that would benefit from such placement, such as the various apical and/or lateral bends.

Figure 3:
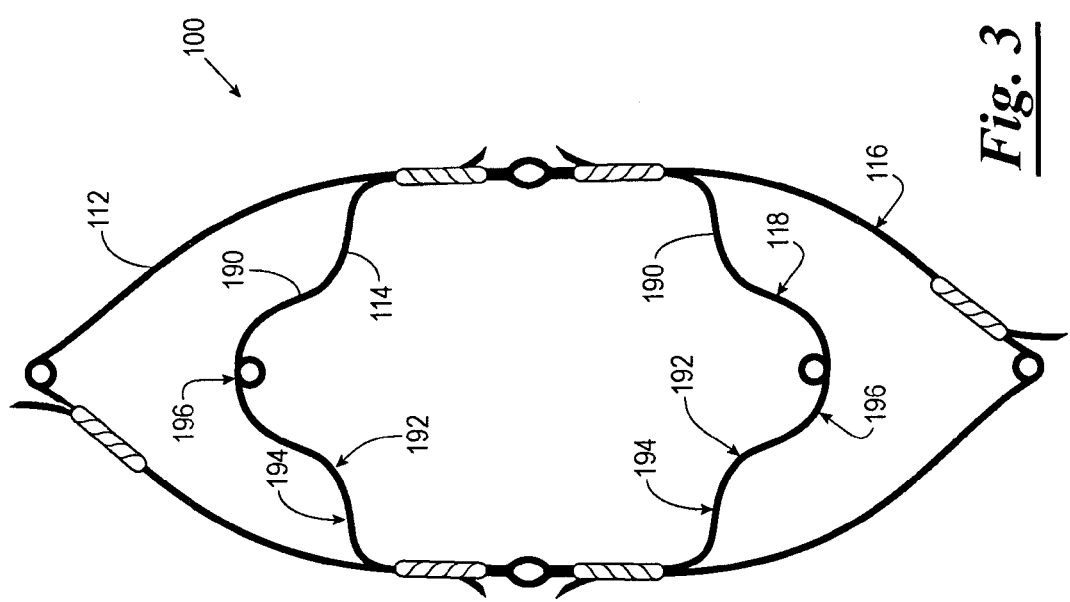
FIG. 3 is an illustration of a support frame according to a second exemplary embodiment shown in a flattened configuration.

FIGS. 3 and 4 illustrate a support frame 110 according to a second exemplary embodiment. The support frame 110 is similar to the support frame 10 illustrated in FIGS. 1 and 2, except as described below. Accordingly, the support frame 110 includes first 112 and second 114 support frames that define first 116 and second 118 closed circumferences. A vessel support portion 170 is defined by the closed circumference 116 of the first support frame 112 and a valve support portion 172 is defined by the closed circumference 118 of the second support frame 114.

In this embodiment, each arm 190 of the second support frame 114 defines an angle 192 to form base 194 and upper 196 portions of the frame member 114. As best illustrated in FIG. 4, which illustrates the support frame 110 in the second configuration, the base portion 194 is a relatively wide portion of the second frame member 114 that extends inward at a first angle relative to a lengthwise axis 198 of the support frame 110. The upper portion 196, in contrast, is relatively narrow and extends inward at a second angle relative to a lengthwise axis 198 of the support frame 110. The second angle is smaller than the first angle. That is, the upper portion 198 of the second frame member 114 extends closer to parallel to the lengthwise axis 198 than the base portion 194. As described below, when a valve is attached to or formed on the valve support portion 172, upper portions of the valve are placed further from the vessel wall than portions adjacent the base portion 194 of the second frame member 114. This is believed to be advantageous at least because the movable portion of the valve, i.e., the portion that defines the valve orifice, is spaced from the vessel wall when implanted in a body vessel.

Any suitable angle can be used for the angle 192. Furthermore, a curvilinear portion can be used in place of a distinct angle. For a specific support frame according to an embodiment of the invention, a skilled artisan can choose a suitable angle based on various considerations, including the desired coaptation length for the valve portion of a valve attached to or formed on the second frame member 114, the desired depth of the valve pockets, and the nature of the vessel wall and the tissue valve or tissue attached to the second frame member 114. It is expressly understood and appreciated that a support frame according to the invention can include a second frame member that has two or more different angles formed on the arms. The use of different angles may be desirable, for example, if a support frame is being used in a biomedical valve designed for use in a body vessel or other location that is not expected to have a uniform inner diameter or that is expected to have differential wall characteristics.

Figure 5:
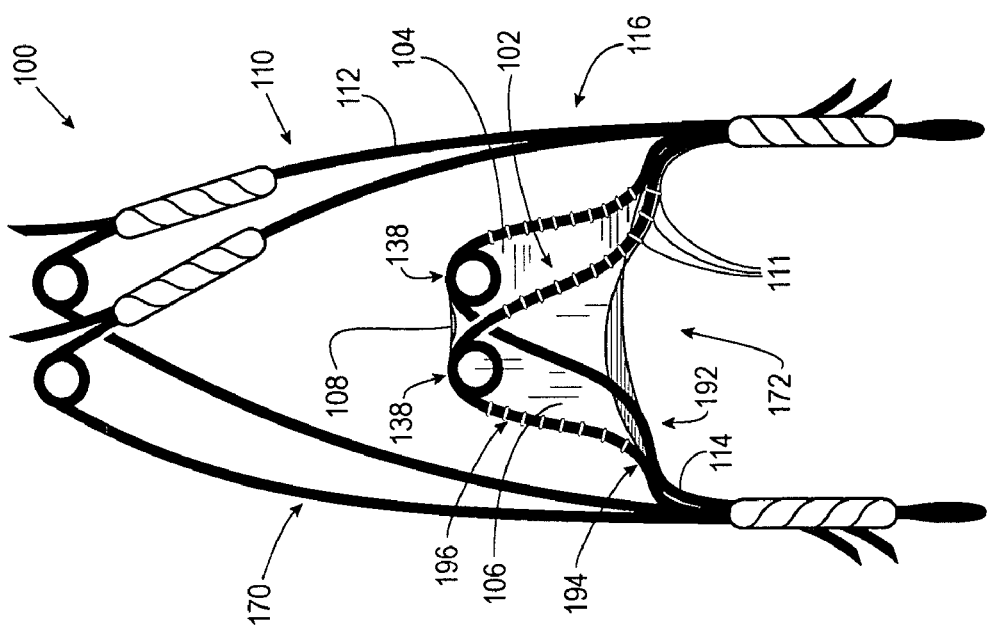
FIG. 5 is a side view of a biomedical valve device that includes the support frame of FIGS. 3 and 4.

FIG. 5 illustrates a biomedical valve 100 that includes the support frame 110 illustrated in FIGS. 3 and 4. A tissue valve 102 is attached to the valve support portion 172 formed by the second support frame 114. The tissue valve 102 includes first 104 and second 106 valve leaflets that cooperatively define a valve orifice 108 that is able to open and close to permit and substantially prevent, respectively, fluid flow through the body vessel into which the biomedical valve 100 is intended to be implanted. As will be described in greater detail below, the tissue valve 102 in this embodiment is an autogenous valve harvested from a different body vessel than the vessel into which the biomedical valve 100 is intended to be implanted. In an alternative embodiment, a valve is formed on the valve support portion 172 by attaching a tissue or portion thereof to the valve support portion in a manner that fashions the attached tissue into a valve. That is, the tissue is attached in a manner defines functional valve that is able to selectively allow and substantially prevent fluid flow through the body vessel. Formation of a valve orifice by two or more valve leaflets, similar to the biomedical valve 100 illustrated in FIG. 5, is an exemplary alternative embodiment.

Any suitable tissue can be used to form a valve of the support frame. The tissue selected for a biomedical valve device according to a particular embodiment of the invention need only be capable of being attached to the support frame in a manner that forms the desired valve configuration. The tissue should be selected to provide desirable behavior of the valve following deployment of the biomedical valve device in a body vessel. Examples of suitable tissues include pleura, such as a lining from the peritoneal cavity, a tissue capsule, such as a renal capsule, and a vessel wall or portion thereof. The use of tissues other than vessel walls might be particularly advantageous when fashioning a biomedical valve device according to an embodiment of the invention that is intended to be implanted in a patient that is missing a particular body vessel or has a damaged portion of a particular body vessel. For example, in humans that have already lost a greater saphenous or other donor vessel, use of a renal capsule or other tissue might be advantageous.

The tissue valve 102 is attached to the second frame member 114 with sutures placed at various positions along the length of the second frame member 114. In this embodiment, sutures 111 placed at the coils 138 disposed at apical bends 128, 130 provide a suitable attachment for the tissue valve adjacent the valve orifice 108. Other suitable means for attaching a tissue valve and/or a tissue to a support frame can be used, of course, including clips, staples, adhesives, tissue welding materials and techniques, and other suitable means for attaching. It will be readily appreciated that the presence of coils 138 at the apical bends 128, 130 of the second frame member 114 is believed to be particularly advantageous at least because, as described above, they provide a mechanism for relieving stress introduced into the support frame 110 by forming the second configuration, and also because they provide a point for securing a tissue valve and/or a tissue to the valve support portion 172.

As will be described in more detail below, biomedical valve devices according to the invention are formed by attaching a tissue valve or a tissue to a support frame. This can be conducted as part of a treatment regimen in which an autogenous tissue valve or tissue is harvested from a patient and immediately attached to an appropriate support frame to form an autogenous biomedical valve. In these methods, it is desirable to conduct the attachment step as quickly as possible to minimize the time during which the harvested tissue valve or tissue is outside of its natural environment.

Figure 6:
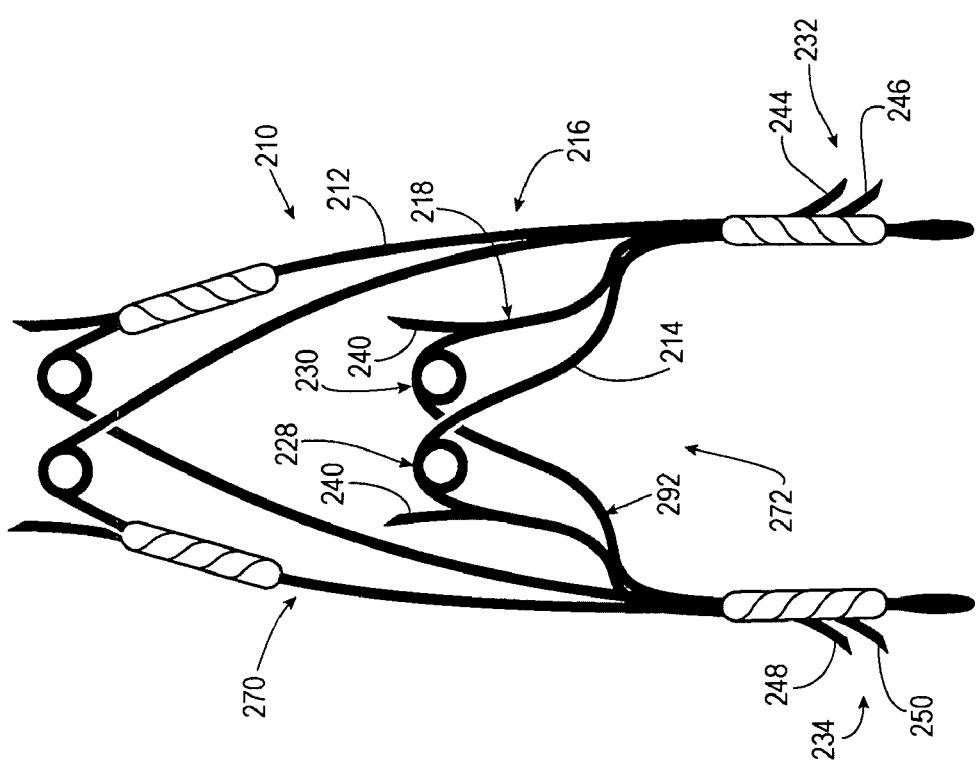
FIG. 6 is a side view of a support frame according to a third exemplary embodiment.

FIG. 6 illustrates a support frame 210 that includes adaptations that are believed to facilitate attachment of a tissue valve or tissue to the support frame in a relatively quick manner. The support frame 210 according to this exemplary embodiment is similar to the support frame 110 illustrated in FIGS. 3 and 4, except as described below. Accordingly, the support frame 210 includes first 212 and second 214 support frames that define first 216 and second 218 closed circumferences. A vessel support portion 270 is defined by the closed circumference 216 of the first support frame 212 and a valve support portion 272 is defined by the closed circumference 218 of the second support frame 214.

Figure 7:
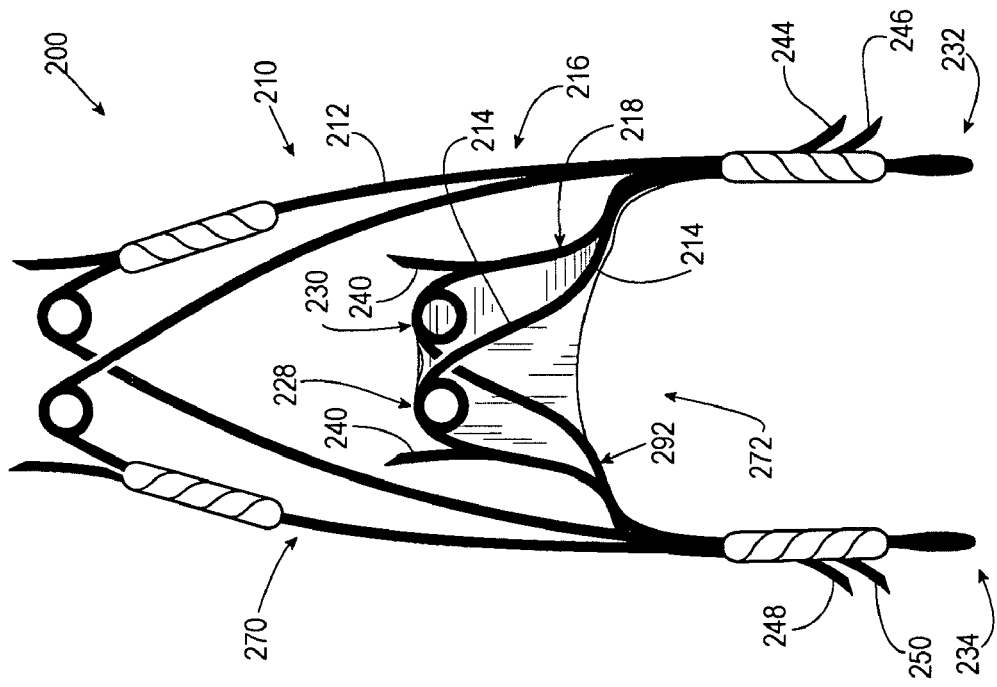
FIG. 7 is a side view of a biomedical valve device that includes the support frame of FIG. 6.

In this embodiment, the second frame member 214 includes barbs 240 disposed at the apical bends 228, 230, in addition to the barbs 244, 246, 248, 250 disposed at lateral bends 232, 234. The positioning of barbs at the apical 228, 230 and lateral 232, 234 bends of the first frame member provide attachment points that allow for relatively quick securement of a tissue valve and/or tissue to the valve support portion 272 during a treatment procedure. A user need only pierce the barbs 244, 246, 248, 250 through the tissue valve and/or tissue to form a biomedical valve device, such as the valve device 200 illustrated in FIG. 7. These adaptations of the support frame 210 are expected to significantly facilitate the use of the support frame as a scaffold for forming biomedical valve devices and to address some of the concerns associated with using autogenous valves in the treatment of various valve disorders, namely, the concern that such an approach necessarily requires time-consuming and complicated valve formation steps.

It is expressly understood and appreciated that sutures and/or other suitable means for attaching a tissue valve and/or tissue to the support frame 210 can be used in addition to the barbs 240, 244, 246, 248, 250. For example, it may be advantageous to include a suture or other means for attaching at an interior point along the length of the second frame member 114, such as at or near the angle 292.

Figure 8:
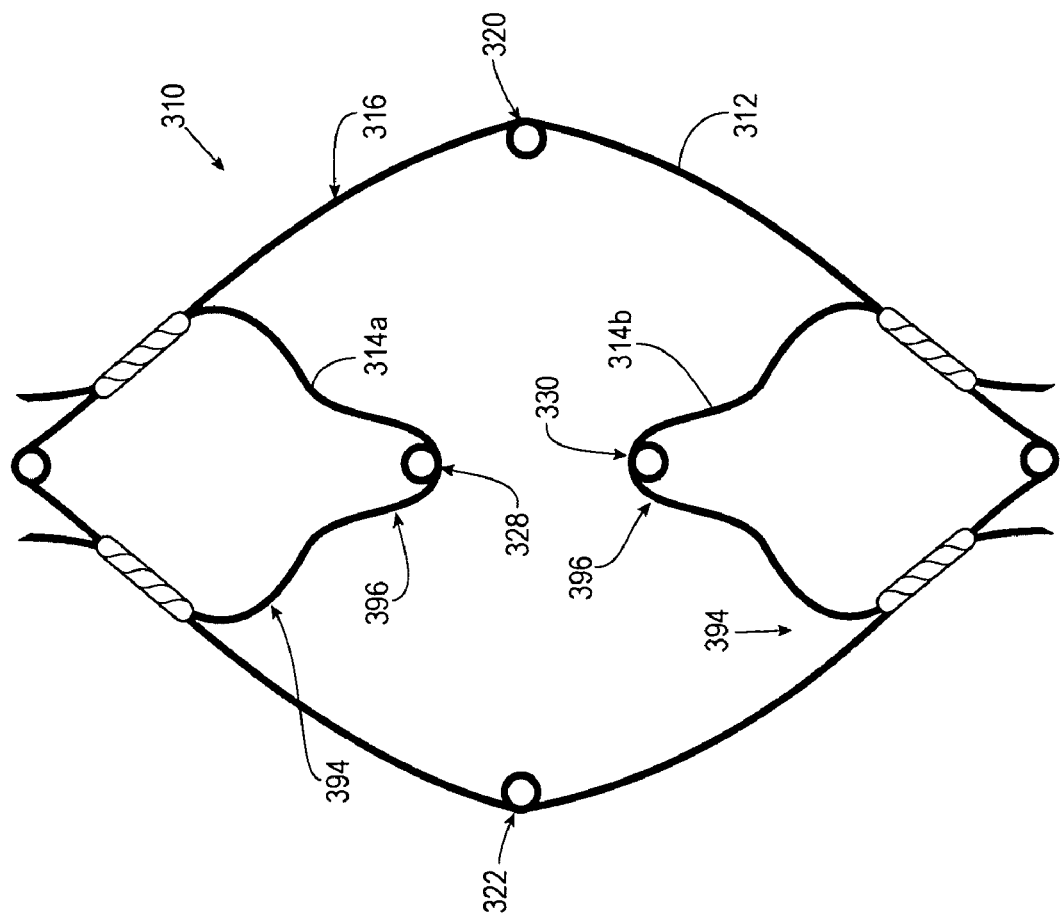
FIG. 8 is an illustration of a support frame according to a fourth exemplary embodiment shown in a flattened configuration.
Figure 10:
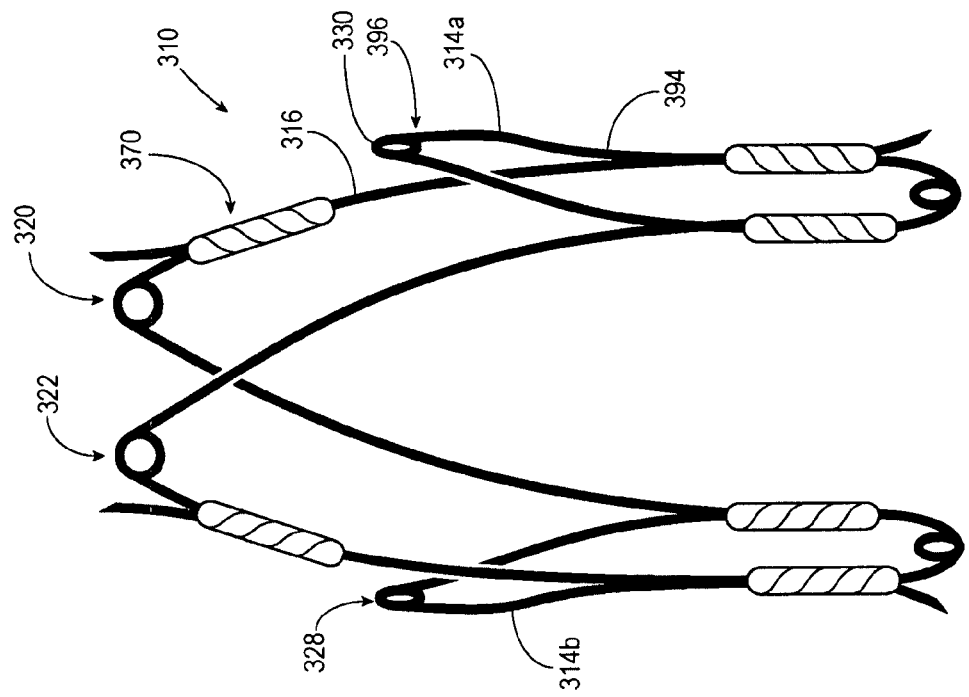
FIG. 10 is a second side view of the support frame of FIG. 8 shown in the second configuration.
Figure 9:
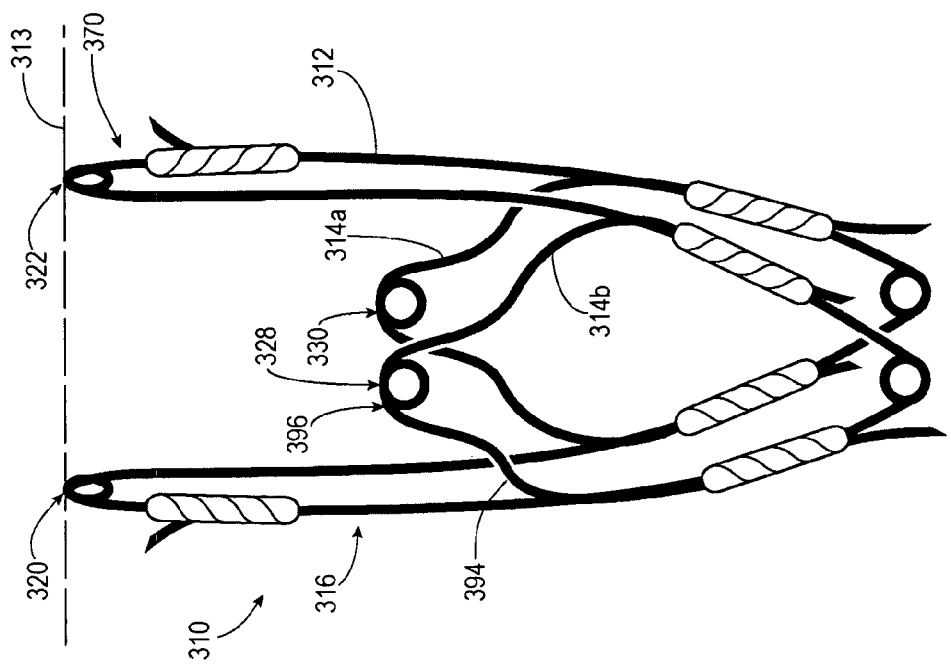
FIG. 9 is a side view of the support frame of FIG. 8 shown in a second configuration.

FIGS. 8 through 10 illustrate a support frame 310 according to another exemplary embodiment. The support frame comprises a first frame member 312 and two secondary frame members 314a, 314b. The first frame member 312 is similar to the first frame member described above in connection with other exemplary embodiments in that it defines a closed circumference 316. The secondary frame members 314a, 314b, however, do not define a single closed circumference by themselves. Rather, in this embodiment, the secondary frame members 314a, 314 beach provide a base 394 and upper 396 portion onto which a tissue valve and/or tissue can be attached to form a biomedical valve device.

In contrast to the second frame members of the embodiments described above, the secondary frame members 314a, 314b of this embodiment are positioned substantially orthogonally to a lateral axis 313 of the first frame member 312. This relative positioning is believed to be advantageous at least because it makes it relatively easier to attach a tissue valve and/or tissue to the tissue support portion during formation of a biomedical valve device, which may reduce the time required for an attachment step during formation of an autogenous valve device. As described above, this reduction in time might prove important to the acceptance of the use of autogenous biomedical valve devices in the treatment of valve conditions, such as venous insufficiency. Furthermore, this relative positioning of the first frame member 312 and the secondary frame members 314a, 314b places the valve orifice of a biomedical valve device that includes the support frame 310 at an angle with respect to a lateral axis of the first frame member 312, such as the lateral axis 313 extending between apical bends 320, 322 of the vessel support portion 370. This positioning is also believed to be advantageous at least because, upon implantation of the biomedical valve device in a body vessel, it is expected to place the valve orifice within a sinus formed in the body vessel due to outwardly directed radial force placed on the vessel wall by the vessel support portion 370. This placement in a formed sinus may facilitate opening and closing of the valve orifice and flushing of the valve pockets. This positioning is best illustrated in FIG. 10.

It is expressly understood and appreciated that the support frame 310 can be modified to include barbs at various locations to facilitate attachment of a tissue valve and/or tissue to form a biomedical valve device, such as at the apical bends 328, 330 of the secondary frame members 314a, 314b, similar to the modifications described above and illustrated in FIGS. 6 and 7.

Figure 12:
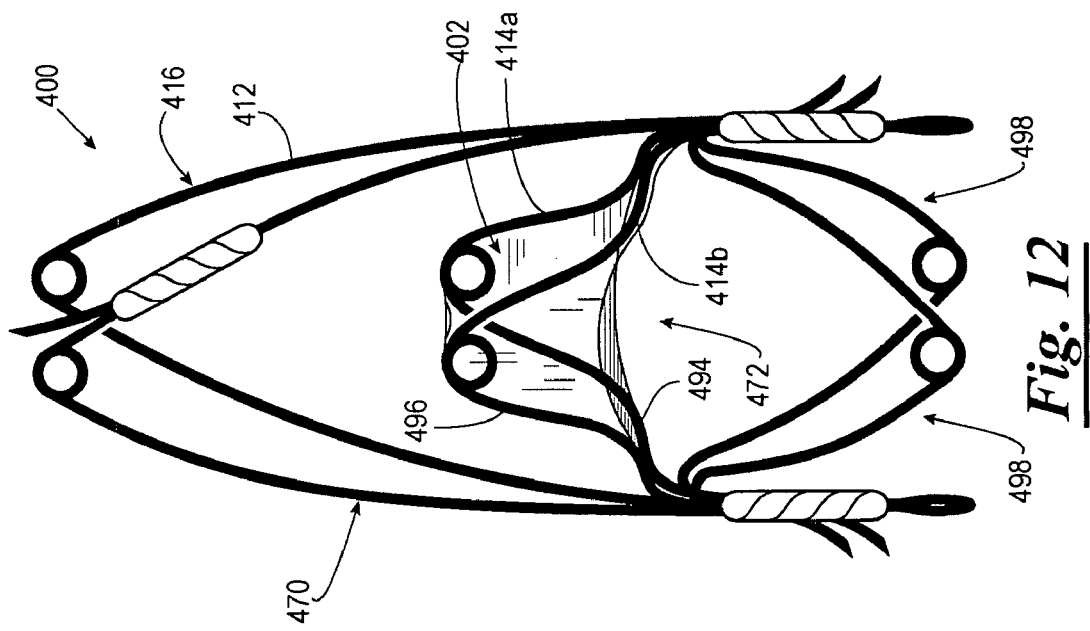
FIG. 12 is a side view of a biomedical valve device that includes the support frame of FIG. 11.
Figure 11:
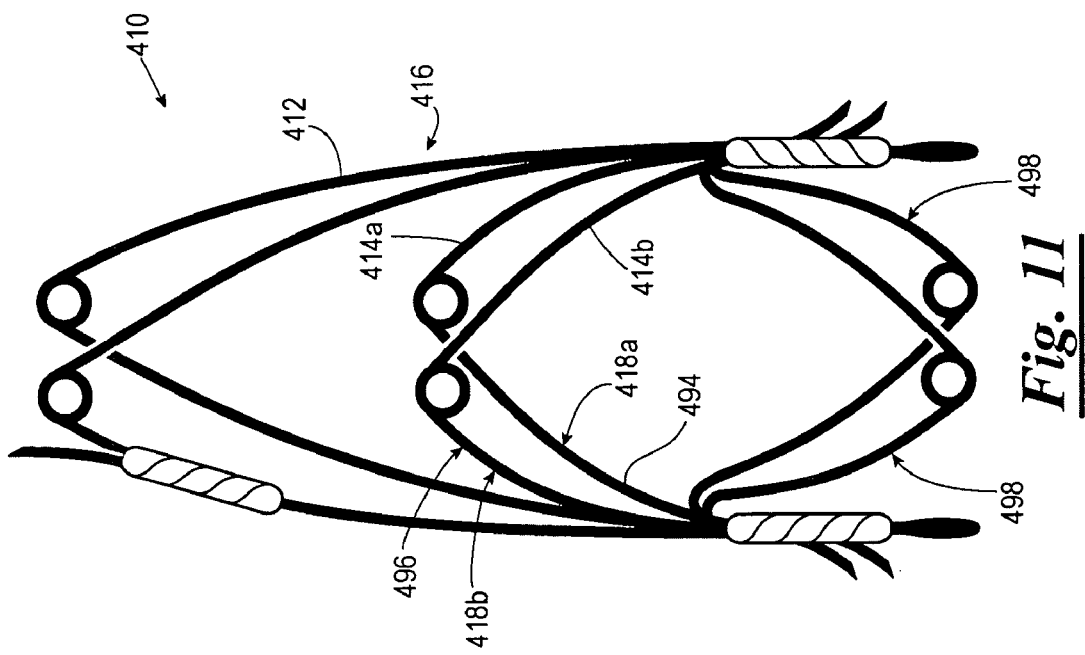
FIG. 11 is a side view of a support frame according to a fifth exemplary embodiment.

FIG. 11 illustrates a support frame 410 according to another exemplary embodiment. The support frame 410 is similar to the support frame 110 described above and illustrated in FIG. 4, except as detailed below. Accordingly, the support frame 410 includes a first frame member 412 that defines a first closed circumference 416. Secondary frame members 414a, 414b are connected to the first frame member 412 and define secondary closed circumferences 418a, 418b. Each of the secondary frame members 414a, 414b includes a base 494, an upper portion 496, and a lower portion 498. When used in a biomedical valve device, such as the device 400 illustrated in FIG. 12, a tissue valve 402 or tissue is attached to a valve support portion 472 defined by the base 494 and upper 496 portions of the secondary frame members 414a, 414b. The lower portions 498 of the secondary frame members 414a, 414b remain substantially free of the tissue valve 402 and/or tissue, as best illustrated in FIG. 12. As such, the lower portions 498 provide a means for providing additional support to the body vessel at the site at which the biomedical valve device is implanted.

The support frame 410 illustrated in FIG. 11 is readily formed by interconnected a first wire form member with second and third wire form members. The first wire form member is formed into the first frame member 412 and the second and third wire form members are individually formed into the secondary frame members 414a, 414b. Connections can be formed using suitable techniques and means for connecting, including cannulae, as described above.

FIGS. 13 and 14 illustrate a support frame 510 according to another exemplary embodiment. The support frame 510 is similar to the support frame 310 described above and illustrated in FIGS. 8 through 10, except as detailed below. Furthermore, the support frame 510 includes a modification similar to the modification made to the support frame 410 illustrated in FIG. 11. That is, the support frame 510 includes a first frame member 512 that defines a first closed circumference 516 and secondary frame members 514a, 514b that define secondary closed circumferences 518a, 518b. Each of the secondary frame members 514a, 514b includes a base 594, an upper portion 596, and a lower portion 598. When used in a biomedical valve device, a tissue valve or tissue is attached to a valve support portion 572 defined by the base 594 and upper 596 portions of the secondary frame members 514a, 514b. The lower portions 598 of the secondary frame members 514a, 514b remain substantially free of the tissue valve and/or tissue. As such, the lower portions 598 provide a means for providing additional support to the body vessel at the site at which the biomedical valve device is implanted.

The support frame 510 according to this embodiment is readily formed in a similar manner to the support frame 410 illustrated in FIG. 11 and described above. The support frame 510 can be formed by interconnecting a first wire form member with second and third wire form members. The first wire form member is formed into the first frame member 512 and the second and third wire form members are individually formed into the secondary frame members 514*a*, 514*b*. Connections can be formed using suitable techniques and means for connecting, including cannulae, as described above.

It is expressly understood and appreciated that any feature or component of any embodiment described herein can be combined with any other embodiment of the invention even though the subject feature or component is not specifically described in connection with such embodiment. For example, the barb adaptations 240 on the second support frame 214 can be used in connection with any embodiment of the invention. The use of these adaptions on a second support frame, or on secondary support frames such as those illustrated in FIGS. 8 through 14 and described above, are believed to be advantageous at least because they facilitate the attachment of a tissue valve and or tissue to the support frame, thereby facilitating the formation of a biomedical valve device.

Furthermore, it is expressly understood and appreciated that, while the support frames described herein are particularly well-suited for use in biomedical valve devices, these apparatuses may find other utility in the medical arts or even in other arts. For example, a support frame according to an embodiment of the invention could likely be adapted to be used as a stent, as an occluder, or as an intravascular filter. Taken alone, the support frames described herein could provide a stenting function to a body vessel. Occluders and filters, among other devices, could be made by adding appropriate functionality to the base support frame, such as an appropriate graft material or wire members. Nothing in this disclosure is intended to limit the scope of the described support frames to the biomedical valves application.

The support frame described herein are particularly well suited for use in biomedical valve devices. A biomedical valve device can be formed by attaching a tissue valve to a valve support portion of a support frame according to the invention using any suitable means for attaching a tissue valve to a support frame, including sutures, barbs, a combination of sutures and barbs, clamps, adhesives, and any other suitable means for attaching. Alternatively, a biomedical valve device can be formed by attaching a tissue, such as a portion of a body vessel, to at least a valve support portion of a support frame according to an embodiment of the invention in a manner that forms a valve capable of permitting flow through a body vessel in a first direction and substantially preventing fluid flow through a body vessel in a second, opposite direction. Tissues can be attached to a valve support portion of a support frame according to the invention using any suitable means for attaching tissue to a support frame, including sutures, barbs, a combination of sutures and barbs, clamps, adhesives, and any other suitable means for attaching. The inventor has determined that barbs, either alone or in combination with another means for attaching, such as sutures, are particularly advantageous when a portion of a body vessel, such as a vein, is used as a tissue in a biomedical valve device according to an embodiment of the invention. The vessel provides a relatively thick material that is able to be pierced by barbs without risking compromise to the tissue and the function of the valve formed by the tissue. As described above, the use of barbs, either alone or in combination with other suitable means for attaching, such as sutures, facilitates the formation of the biomedical valve device, which can be particularly advantageous when the formation is part of a time sensitive procedure, such as formation of an autogenous biomedical valve device.

Methods of making biomedical valve devices are provided. An exemplary method comprises the steps of providing a support frame according to the invention and providing a tissue valve. Another step comprises attaching the tissue valve to the support frame as described above. In one exemplary embodiment, the tissue valve comprises a venous valve. In another exemplary embodiment, the tissue valve comprises a venous valve harvested from the same patient into which the biomedical valve device is intended to be implanted. In this embodiment, the biomedical valve device comprises an autogenous biomedical valve device.

An alternative method of making a biomedical valve device comprises the steps of providing a support frame according to the invention and providing a tissue. Another step comprises attaching the tissue valve to the support frame as described above. In one exemplary embodiment, the tissue comprises a portion of a body vessel. In another exemplary embodiment, the tissue comprises a portion of a vein. In another exemplary embodiment, the tissue comprises a portion of a vein harvested from the same patient into which the biomedical valve device is intended to be implanted. In this embodiment, the biomedical valve device comprises an autogenous biomedical valve device.

In another exemplary embodiment, the tissue comprises a portion of a vessel that includes a native valve. The vessel is attached to the support frame in an inverted orientation, placing the valve on the exterior of the support frame. Another portion of the tissue is fashioned into a valve. When deployed in a body vessel, the native valve is diposed adjacent the interior vessel wall. This is believed to be advantageous at least because it offers a simple fabrication process. Furthermore, the presence of the native valve adjacent the vessel wall following deployment may enhance anchoring of the biomedical valve device within the body vessel.

Figures 15, 16:
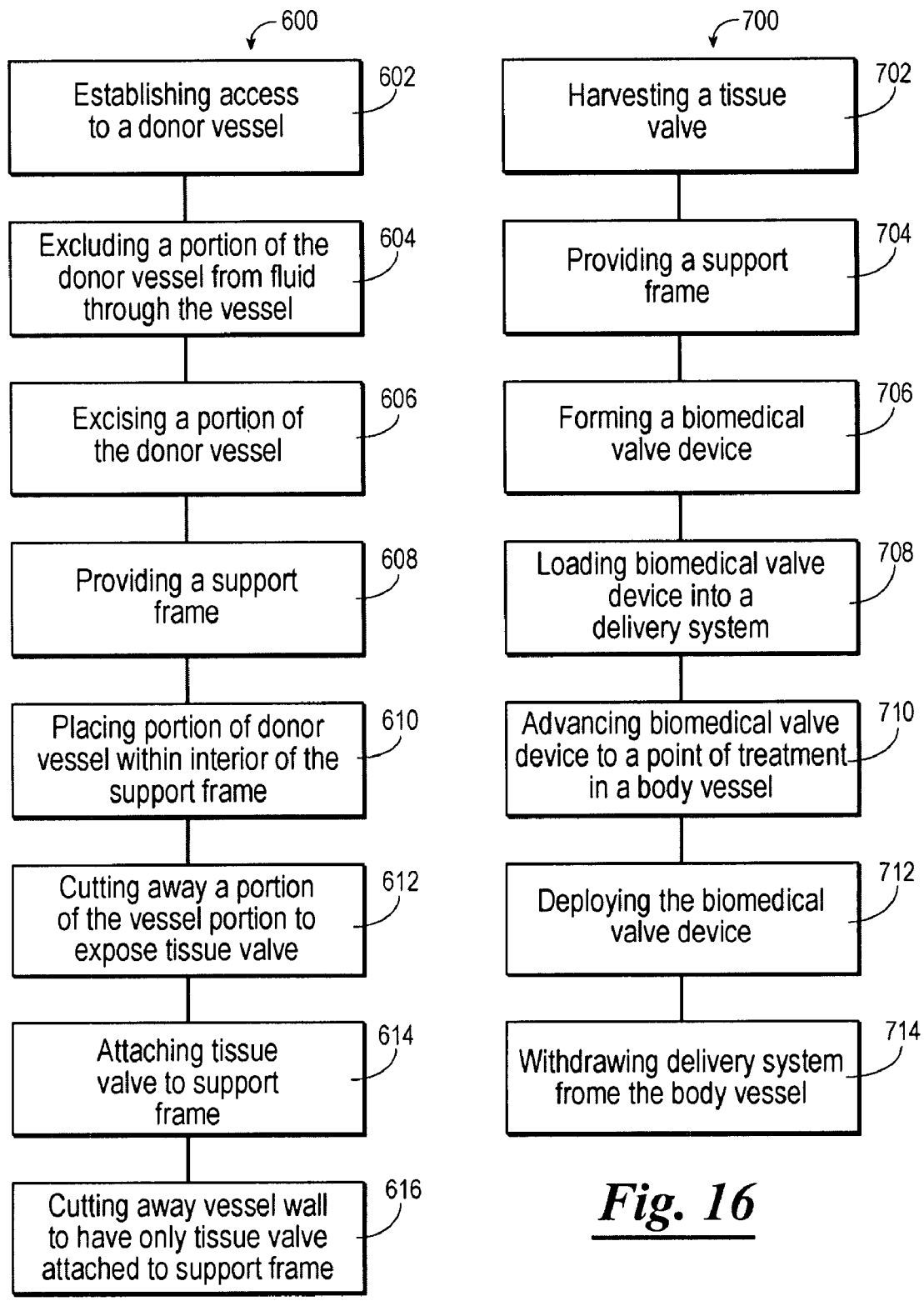
FIG. 15 is a flowchart illustrating an exemplary method of making an autogenous biomedical valve.
FIG. 16 is a flowchart illustrating an exemplary method of treating an animal for a valve-related condition.

FIG. 15 illustrates an exemplary method 600 of making an autogenous biomedical valve device according to the invention. An initial step 602 comprises establishing access to a donor vessel. For this exemplary method and step, the term "donor vessel" refers to a body vessel of the same patient into which the autogenous biomedical valve device is intended to be implanted. Any suitable vessel can be used. This exemplary method makes use of a preexisting natural valve, so the vessel should be selected to include such a valve. A suitable vein is appropriate. Jugular veins have been used in animal studies.

Another step 604 comprises excluding a portion of the donor vessel from fluid flow through the vessel. This can be accomplished by tying or clamping off a portion of the donor vessel as is known in the art. Another step 606 comprises excising a portion of the donor vessel from the patient. For this exemplary method, the portion is selected to include a native tissue valve, such as a native venous valve. The remaining vessel is advantageously tied, clamped or otherwise sealed off to prevent unintended leakage of fluid following removal of the portion to be used for forming the autogenous biomedical valve device. Following removal of the portion of the body vessel that includes the tissue valve, the portion is advantageously kept hydrated with fluid from the vessel or an appropriate tissue preservation fluid, such as University of Wisconsin solution known in the art. The portion is advantageously kept tied, clamped, or otherwise sealed until later in the method, as described below.

Another step 608 comprises providing a support frame according to the invention. Any suitable support frame according to the invention can be used in the method, and the specific support frame selected for a particular method according to the invention will depend on several considerations, including the nature of the tissue valve and donor vessel being used and the nature of the body vessel into which the autogenous biomedical valve device will be implanted.

Another step 610 comprises placing the portion of the donor vessel within the interior of the support frame such that the tissue valve is substantially adjacent the valve support portion of the support frame. Another step 612 comprises cutting away a portion of the body vessel portion to expose the tissue valve. Another step 614 comprises attaching the tissue valve to the valve support portion of the support frame. In this step, any suitable means for attaching the tissue valve to the support frame can be used, including sutures, clamps, and other suitable means for attaching. The inventor has determined that the use of barbs formed on the tissue support portion of the support frame, with or without other means for attaching the tissue valve to the support frame, provides significant advantage in that barbs provide a relatively quick and secure way to attach the tissue valve to the support frame, significantly reducing complexity and time involved in the formation of the autogenous biomedical valve device.

An optional step 616 comprises cutting away the vessel wall to leave substantially only the tissue valve attached to the support frame. An alternative to this optional step comprises securing one or more portions of the vessel wall to a portion of the support frame, such as the vessel support portion.

In one alternative method, the step of placing the portion of the donor vessel within the interior of the support frame is eliminated. Instead, a step according to this method comprises placing the support frame within the lumen of the body vessel such that the tissue valve is substantially adjacent the valve support portion of the support frame. This can be accomplished by opening one end of the portion of the body vessel that includes the tissue valve and advancing the support frame into the lumen of the portion. Positioning of the tissue valve can be verified by shining a light directly on the body vessel and observing the support frame position through the vessel wall. Observation can be enhanced by applying pressure, such as with a finger, to effectively compress or thin the vessel wall under the light source.

Methods of treating animals for valve-related conditions are also provided. Biomedical valve devices according to the invention are particularly well-suited for treating a variety of valve-related conditions, including venous insufficiency and heart valve conditions. The support frame according to the invention provide a scaffold onto which a valve can be attached or formed, and enable the use of percutaneous delivery techniques to deploy the biomedical valve devices with a body vessel of an animal, including humans. The use of autogenous biomedical valve devices in methods according to the invention are considered particularly advantageous because they significantly reduce various materials-related issues associated with implanting a biomedical valve device within a body vessel.

FIG. 16 illustrates one exemplary method 700 of treating an animal, such as a human, for venous insufficiency. An initial step 702 comprises harvesting a tissue valve from the patient. Another step 704 comprises providing a support frame according to the invention. Another step 706 comprises forming an autogenous biomedical valve device by attaching the tissue valve to the support frame. Any suitable method of forming a biomedical valve device according to the invention can be used for this step.

Another step 708 comprises loading the biomedical valve device into a delivery system. Any suitable delivery system can be used and the specific delivery system selected for a particular method will depend on several considerations, including the nature of the tissue valve, the overall profile of the biomedical valve device, and the nature of the vessel into which the biomedical valve device is intended to be implanted. Those skilled in the art will be able to readily identify a suitable delivery system for use in the method. Examples of suitable delivery systems are described in International application PCT/US05/30861, entitled DELIVERY SYSTEM WHICH FACILITATES HYDRATION OF AN INTRALUMINAL MEDICAL DEVICE, the entire disclosure of which is incorporated into this disclosure in its entirety for the purpose of describing suitable delivery systems for use with the support frames and biomedical valve devices described herein.

Another step 710 comprises advancing the biomedical valve device, loaded on the delivery system, to a point of treatment within a body vessel. Another step 712 comprises deploying the biomedical valve device using a technique appropriate for the selected delivery system. Another step 714 comprises withdrawing the delivery step from the body vessel.

An alternative method of treating an animal includes an initial step of implanting a support frame according to the invention in a body vessel adjacent a natural valve. Next, the support frame is kept in the body vessel for a period of time sufficient in length to allow the support frame to become sufficiently integrated into at least a portion of the thickness of the vessel wall at the point of implantation. The support frame is advantageously allowed to become sufficiently integrated into the wall thickness such that the support frame fully supports the natural valve upon excision of the portion of the vessel that contains the valve. An period of approximately 14 days is considered appropriate when sheep valves are used, although any suitable time period can be used.

Following the passage of the sufficient time period, the portion of the body vessel that contains the support frame and natural valve is harvested. Then, the support frame/natural valve combination, which can be referred to as a valve device, is loaded into an appropriate delivery system and implanted at a desired point of treatment, such as at a fixed distance from a natural valve shown to be or suspected of being incompetent, or adjacent a natural valve shown to be or suspected to be incompetent.

Optional steps in this exemplary method include inspecting the valve device for ruggedness or other desired property; alteration of the valve device following the harvesting step, such as by securing the valve and/or a portion of the vessel to the support frame using a suitable means of securement. Also, a step of hydrating the valve device following harvesting and prior to loading in the delivery system and/or prior to implanting at the treatment site.

Implantation can also be accomplished surgically, in which case the loading step can be eliminated.

The initial implantation step can be performed in the same animal, including a human patient, as the animal in which the valve device is ultimately implanted. Alternatively, a different animal, and indeed a different species, can be used. For example, the initial implantation step can be performed in a sheep, and the valve device implantation step can be performed in a human patient. In this case, a sheep valve is implanted in a human patient. In any method in which different animals and/or species are used in the two implantation steps, standard tissue grafting considerations should be evaluated and addressed.

The foregoing detailed description provides exemplary embodiments of the invention and includes the best mode for practicing the invention. The description and illustration of embodiments is intended only to provide examples of the invention and not to limit the scope of the invention, or its protection, in any manner.

I claim:

1. A biomedical valve device for implantation in a body vessel of an animal in need thereof, said valve device having first and second ends and a lengthwise axis extending from the first end to the second end, comprising:

a first frame member comprising a first wire member formed into a first closed circumference having a first length and defining a vessel support portion of said biomedical valve device, the first frame member defining first and second apical bends positioned on a first transverse axis that is perpendicular to said lengthwise axis and first and second lateral bends positioned on a second transverse axis that is perpendicular to said lengthwise axis and to the first transverse axis, the vessel support portion having a first axial length extending along said lengthwise axis of said biomedical valve device from said first end to said second end;

a second frame member comprising a second wire member having first, second, third, and fourth arms formed into a second closed circumference having a second length and defining a valve support portion of said biomedical valve device, the second length being less than the first length, each of the first, second, third, and fourth arms defining an angle to form an arm base portion and an arm upper portion, the arm base portions cooperatively defining a valve base portion and the arm upper portions cooperatively defining a valve upper portion, the second frame member defining third and fourth apical bends positioned on a third transverse axis that is perpendicular to said lengthwise axis and on a plane containing the first transverse axis, and third and fourth lateral bends positioned on the second transverse axis, the valve support portion having a second axial length extending along said lengthwise axis of said biomedical valve device and between said first and second ends;

a tissue valve attached to the valve base portion and valve upper portion defined by the first, second, third, and fourth arms of the second frame member, the tissue valve comprising first and second valve leaflets that cooperatively define a valve orifice extending between the third and fourth apical bends;

a first cannula connecting the first and third lateral bends such that the first and third lateral bends are positioned at the first end of said valve device; and a second cannula connecting the second and fourth lateral bends such that the second and fourth lateral bends are positioned at the first end of said valve device;

wherein the first axial length is greater than the second axial length;

wherein the first frame member and the second frame member are interconnected by the first and second cannulae such that the valve orifice is positioned within the first closed circumference; and wherein the arm base portion of each of the first, second, third, and fourth arms of the second frame member extends inward toward said lengthwise axis at a first angle relative to said lengthwise axis and the arm upper portion of each of the first, second, third, and fourth arms of the second frame member extends inward toward said lengthwise axis at a second angle relative to said lengthwise axis such that the valve upper portion is narrower than the valve base portion and such that the valve orifice is spaced from an inner wall of said body vessel when said biomedical valve device is implanted therein.

2. The biomedical valve device according to claim 1, wherein the first frame member is formed from a single wire member.

3. The biomedical valve device according to claim 2, wherein the first frame member defines at least one coil in at least one of the apical and lateral bends.

4. The biomedical valve device according to claim 1, wherein the second frame member is formed from a single wire member.

5. The biomedical valve device according to claim 4, wherein the second frame member defines at least one coil in at least one of the apical and lateral bends.

6. The biomedical valve device according to claim 1, further comprising at least one barb disposed on at least one of the first and second frame members.

7. The biomedical valve device according to claim 1, wherein the tissue valve comprises an autogenous valve harvested from said animal.

8. The biomedical valve device according to claim 1, wherein the tissue valve comprises a valve harvested from a different animal of the same species as said animal.

9. The biomedical valve device according to claim 8, wherein said animal is a human.

10. The biomedical valve device according to claim 1, wherein the tissue valve comprises a valve harvested from a different animal of a different species than said animal.

11. The biomedical valve device according to claim 10, wherein said animal is a human.

12. The biomedical valve device according to claim 1, wherein each of the first frame member and the second frame comprises metal.

13. The biomedical valve device according to claim 12, wherein each of the first frame member and the second frame comprises stainless steel.

14. The biomedical valve device according to claim 12, wherein each of the first frame member and the second frame comprises a superelastic alloy.

15. The biomedical valve device according to claim 14, wherein each of the first frame member and the second frame comprises nitinol.

16. The biomedical valve device according to claim 1, wherein each of the first frame member and the second frame comprises a polymeric material.

17. The biomedical valve device according to claim 1, wherein each of the first frame member and the second frame comprises a resorbable material.

18. The biomedical valve device according to claim 1, wherein the tissue valve is formed from pleura.

19. The biomedical valve device according to claim 1, wherein the tissue valve is formed from a tissue capsule.

20. The biomedical valve device according to claim 1, wherein the tissue valve is formed from a vessel wall.

* * * * *